(12) United States Patent
Schwarz et al.

(10) Patent No.: US 7,468,800 B2
(45) Date of Patent: Dec. 23, 2008

(54) METHOD AND APPARATUS FOR DETERMINING SURFACE PROPERTIES

(75) Inventors: Peter Schwarz, Königsdorf (DE);
Gerhard Hentschel, Lenggries (DE);
Konrad Lex, Königsdorf (DE)

(73) Assignee: BYK-Gardner GmbH (DE)

( * ) Notice: Subject to any disclaimer, the term of this patent is extended or adjusted under 35 U.S.C. 154(b) by 225 days.

(21) Appl. No.: 11/421,023

(22) Filed: May 30, 2006

(65) Prior Publication Data
US 2006/0274317 A1 Dec. 7, 2006

(30) Foreign Application Priority Data
Jun. 2, 2005 (DE) ........................ 10 2005 025 291

(51) Int. Cl.
*G01B 11/28* (2006.01)
(52) U.S. Cl. ........................ 356/630; 356/425; 356/634
(58) Field of Classification Search ... 356/237.1–237.5, 356/445–446, 600, 239.1–239.3, 630–632, 356/425
See application file for complete search history.

(56) References Cited

U.S. PATENT DOCUMENTS

| | | | | |
|---|---|---|---|---|
| 4,929,846 | A * | 5/1990 | Mansour | 250/559.07 |
| 6,313,913 | B1 * | 11/2001 | Nakagawa et al. | 356/237.2 |
| 2002/0093648 | A1 * | 7/2002 | Nikoonahad et al. | 356/237.1 |
| 2006/0033922 | A1 | 2/2006 | Sperling et al. | 356/446 |
| 2006/0065857 | A1 | 3/2006 | Lex | 250/559.4 |
| 2006/0092417 | A1 | 5/2006 | Schwarz et al. | 356/337 |
| 2006/0119854 | A1 | 6/2006 | Sperling et al. | 356/446 |

* cited by examiner

*Primary Examiner*—Hoa Q Pham
(74) *Attorney, Agent, or Firm*—Hayes Soloway P.C.

(57) ABSTRACT

A method of determining surface properties is provided, in which radiation is irradiated onto a first region of a surface to be examined, then at least some of the radiation irradiated onto the first region and returned by the latter is detected, and a measured value characteristic of this returned radiation is output. In a further step, the radiation is irradiated onto a second region of the surface and once again at least some of the radiation irradiated onto the second region and returned by the latter is detected, and a second measured value characteristic of this radiation is output. Finally, a result value is output which is characteristic of a relationship between the first measured value and the second measured value.

24 Claims, 1 Drawing Sheet

METHOD AND APPARATUS FOR DETERMINING SURFACE PROPERTIES

Figure 1:
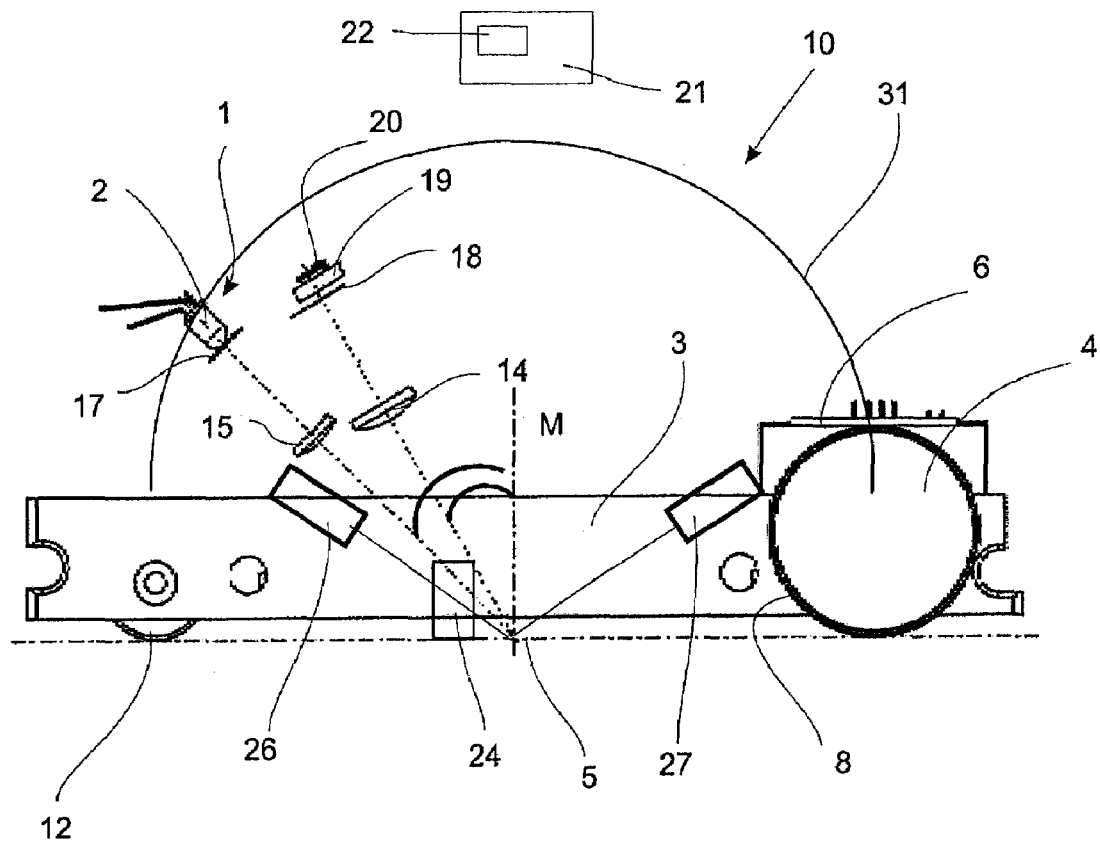

The present invention relates to a method and an apparatus for determining surface properties such as, in particular but not exclusively, the colour of the surface.

The invention is described with reference to surfaces of motor vehicles. However, it should be pointed out that the invention may also be used in the case of other surfaces, such as for example the coatings of items of furniture, of floor coverings and the like.

The optical appearance of objects or of the surfaces thereof, particularly of surfaces on motor vehicles, is largely determined by the surface properties thereof. Since the human eye is suitable only to a limited extent for objectively determining surface properties, there is a need for aids and apparatuses for the qualitative and quantitative determination of surface properties.

In this case, surface properties such as shine, orange peel, colour, macrostructure or microstructure, image sharpness, brightness haze, surface structure and/or surface topography and the like are determined.

From the prior art, apparatuses are known in which a radiation device projects radiation onto the measurement surface to be examined, and the radiation that is reflected and/or scattered by this measurement surface is detected by a detector and evaluated.

When coating motor vehicle or bodywork surfaces, the problem often arises that certain partial areas of the bodywork are coated differently than other areas. It may happen for example that a painting device paints certain areas of the motor vehicle twice but paints other areas only once, and in this way a different overall colour appearance is produced in different areas. This different colour appearance on individual areas of the surface can be objectively discerned only with difficulty by the human eye since it depends on many boundary conditions such as, for example, the irradiated light, the viewing angle and the like.

It is therefore an object of the present invention to provide a method and an apparatus which gives objective information about the uniformity of a colour layer on an object. According to the invention, this is achieved by a method according to claim 1 and by an apparatus according to claim 9. Advantageous embodiments and further developments form the subject matter of the dependent claims.

In the method according to the invention for determining surface properties, in one method step radiation is irradiated onto a first region of a surface to be examined. In a further method step, at least some of the radiation irradiated onto the first region and returned by the latter is detected, and a signal characteristic of this radiation or a characteristic first value is output. In a further step, radiation is irradiated onto a second region of the surface which is different from the first region. Once again, at least some of the radiation irradiated onto the second region and returned by the latter is detected, and a second value characteristic of this returned radiation is output. Finally, according to the invention, a result value is output which is characteristic of a relationship between the first value and the second value.

The term radiation is to be understood as meaning any type of radiation, such as for example infrared light, UV light, light in the visible wavelength region, X-ray radiation and the like. The radiation used is preferably light in the visible region and particularly preferably a standardized white light.

The term returned radiation is to be understood as meaning, in particular but not exclusively, radiation that has been scattered at any angle, but also reflected radiation.

A property which is characteristic of the radiation is to be understood as meaning, in particular but not exclusively, the intensity, spectral region, wavelength or polarization thereof or else a combination of these properties.

A characteristic value is to be understood as meaning a value for at least one of these properties.

Preferably, the distance between the first region and the second region is also measured. Here, in particular but not exclusively, a predefined point of the first and of the second region is selected, such as for example the geometric centre point, and the distance between these two points is measured. By virtue of this measurement of the distance, it is possible to assign measured values or measured signals to specific locations on the surface of the bodywork.

The radiation is preferably irradiated successively onto a large number of different regions of the surface. This means that the radiation is respectively irradiated onto the different regions and in each case the recorded measured values are stored one after the other, wherein this preferably takes place with an assignment to the respective geometric location based on the measured distance. For measurement purposes, the apparatus is preferably moved relative to the surface at least intermittently essentially along a substantially straight line. This movement line may also be determined by contours of the examined surface, for example as in the case of a motor vehicle door. In this way, a profile of values along this line can be recorded, and it can be ascertained whether the optical appearance and, in particular but not exclusively, the colour appearance of the surface changes along this line.

Furthermore, the result value is preferably selected from a group of result values which contains arithmetic mean values, geometric mean values, scatterings, variances, differences, differential quotients, maxima, minima or combinations thereof. As mentioned above, the object of the invention is to provide the user with an objective measure of the uniformity of the surface coating. For this reason, scatterings, variances or differences are advantageously particularly suitable as result values since such result values are a direct measure of the uniformity of a coating of the surface to be examined.

For example, a scattering value of "0" would be characteristic of a completely uniform surface. The difference between a maximum first value and a minimum second value in the case of a large number of recorded values could also be used as a further measure of the uniformity of the surface coating. By virtue of the above-described simultaneous recording of the distance between the individual regions, it is furthermore possible to precisely locate those regions of the surface in which the coating is particularly non-uniform.

Preferably, a number of measurements are carried out along a number of lines which are essentially parallel to one another, so that in this way a complete partial region of a motor vehicle surface, such as a complete region of a motor vehicle door for example, can be measured. By virtue of the recording of the individual measured values, which preferably takes place with an assignment to the geometric location, it is possible to create a profile of the motor vehicle surface, preferably by using processors or computers, said profile providing information about those regions in which the colour is distributed in a non-uniform manner. In this way, a corresponding three-dimensional profile of the surface to be examined can also be created.

Preferably, a layer thickness of the surface to be examined is determined. Particularly preferably, the layer thickness is measured in each case in the different regions and essentially at the same time as the optical properties. In this way, both a measured value for the layer thickness and a measured value for the characteristic surface property can be assigned to a specific region of the surface. This measurement of the layer thickness can be determined via optical elements, via inductive sensors and the like.

A corresponding layer thickness measurement device for examining the measurement surface may be in touching contact with the surface or else may operate in a contactless manner.

Preferably, the radiation is irradiated onto the surface at a predefined angle. Particularly preferably, this is an angle of essentially 45° with respect to a direction perpendicular to the surface, since this angle is standardized for comparable measurement methods.

The radiation device may irradiate both directional and non-directional radiation onto the surface. The detection of the light or radiation returned by the surface likewise takes place at a predefined angle. This angle is preferably sufficiently remote from the reflection angle and is with particular preferably around 20°-40° with respect to the direction perpendicular to the surface. This is explained in more detail with reference to the figures.

Preferably, the radiation is guided onto the surface via diffraction elements such as lenses and the like. In addition, use is preferably made of filter elements in order to filter the radiation according to its spectral components.

The present invention furthermore relates to an apparatus for determining surface properties. This apparatus has at least a first radiation device with at least one radiation source, which emits radiation onto a surface to be examined. In addition, there is at least one radiation detector device which detects at least some of the radiation that has been emitted by the at least one radiation device and has then been returned by the measurement surface, and outputs at least one measured signal or one measured value which is characteristic of the reflected and/or scattered radiation. According to the invention, a processor device is provided which compares at least two measured signals output by the measurement device, which signals correspond to different locations on the surface, and outputs a value characteristic of this comparison.

Preferably, the apparatus has a movement device in order to move the apparatus relative to the surface along a predefined movement direction which is preferably essentially rectilinear. With particular preference, this involves at least one wheel arranged on the apparatus. Preferably two or particularly preferably four wheels are provided in order to move the apparatus relative to the surface. This movement device is preferably configured in such a way that on the one hand it does not damage, for example scratch, the surface during the movement, and on the other hand it is ensured that the movement device does not slide but rather rolls with respect to the surface.

Preferably, a memory device is provided in order to store a large number of measured signals and/or values derived from these measured signals. Either the signals themselves may be stored or else values output by the radiation detector device, such as voltage values or the like for example.

The radiation device is preferably arranged at a predefined angle with respect to the surface to be examined, and this angle is particularly preferably 45° with respect to the perpendicular direction relative to the surface. This angle is a standard angle, so that comparisons with other devices are possible.

In another preferred embodiment, a large number of radiation detector devices are provided which are arranged at different angles with respect to the surface. In this embodiment, there is accordingly provided one radiation device and a large number of radiation detector devices. On the other hand, it is also possible to provide a large number of radiation devices which are arranged at different angles with respect to the surface and one radiation detector device which is arranged at a specific angle with respect to the surface. In this way, the behaviour of the surface when it is irradiated at different angles can be observed. Preferably, at least one radiation detector device is arranged at an angle of between 20° and 40°, preferably between 25° and 35° and particularly preferably around 30°, with respect to a direction perpendicular to the surface.

In principle, the radiation detector device could also be arranged at considerably greater angles with respect to the direction perpendicular to the surface, such as at an angle of 70° for example. However, arranging it at a relatively small angle has the advantage that curvatures of the surface to be examined have only a slight effect on the measurement result.

Preferably, all the values output by each of the radiation detector devices are stored in the memory device.

In another preferred embodiment, a large number of radiation devices are arranged essentially perpendicular to the movement direction of the apparatus and essentially parallel to the surface to be examined, that is to say essentially at the same level. This means that a predefined number of radiation devices are arranged next to one another, namely on a line essentially perpendicular to the movement direction of the apparatus relative to the surface. By virtue of this large number of radiation devices, a relatively large area of the surface can be examined at the same time by moving the apparatus relative to the surface.

Instead of arranging a large number of radiation devices, or in addition to doing so, it is also possible to use suitable optical elements such as cylindrical lenses in order to illuminate a relatively large area in a direction perpendicular to the movement direction of the apparatus relative to the surface.

In another preferred embodiment, a large number of radiation detector devices are arranged next to one another essentially perpendicular to the movement direction of the apparatus. In this way, radiation detector devices which are accordingly arranged next to one another correspond to the respective radiation devices arranged next to one another. Preferably, the beam paths between the individual radiation devices and the corresponding radiation detector device are at least partially screened off from one another.

In another preferred embodiment, the apparatus has a path length measurement device in order to determine the length of the path travelled relative to the surface. In this way, as mentioned above, a number of measurement points can be recorded and these can be assigned to specific locations on the surface. In this way, it is possible to create an overall image of the surface.

Preferably, at least one radiation device has at least one radiation source which is selected from a group of radiation sources comprising thermal radiation sources, such as, in particular but not exclusively, incandescent lamps, halogen lamps, coherent and non-coherent semiconductor radiation sources, gas discharge radiation sources, lasers, combinations thereof and the like. Particularly preferably, use is made of a radiation source which emits white light and in particular standardized white light. The use of a white light-emitting diode is also to be regarded as particularly preferred.

In a further preferred embodiment, the apparatus has a layer thickness measurement device. This layer thickness measurement device may comprise, as mentioned above, inductive measurement elements, capacitive measurement elements and the like.

In a further preferred embodiment, the apparatus has at least one filter element in order to select a predefined component of the radiation. Particularly preferably, this comprises filter elements which let through certain spectral components of the radiation but block others. In this way, it is possible to carry out an examination of the surface properties in a manner resolved according to colour. Moreover, dispersive elements such as grids, prisms and the like may be provided in the beam path between the radiation device and the radiation detector device.

In a further preferred embodiment, a calibration device is provided which allows the apparatus to be oriented with respect to the surface. This embodiment is based on the problem that the measurement result may be falsified if the apparatuses tilt relative to the surface, since the radiation can then no longer be irradiated onto the detector device at the standardized angle and thus the measurement results may be falsified.

This calibration device may for example comprise a laser which emits light at a predefined angle onto the surface to be examined. The light of the laser which is reflected by the surface is detected by a detector device and the location at which the laser radiation strikes the surface of the detector device is determined. By determining this location, the user can be informed as to how he must tilt the apparatus relative to the surface or as to the angle at which the apparatus is inclined compared to a desired value.

A calibration device comprising a software filter could also be provided. In this case, the location at which reflected radiation strikes is likewise determined in a detector device, and this location is placed in relation to a desired location. From this relation, the tilting of the apparatus relative to the surface is calculated and the measured values are adapted or calibrated accordingly.

Moreover, a number of proximity sensors may be provided which measure the distance of selected reference points of the apparatus from the surface and in this way indicate to the user how the apparatus must be oriented with respect to the surface.

In a further preferred embodiment, the apparatus according to the invention has a processor device which outputs, from the measured signals or values, a value which is characteristic of the comparison. Here, the processor device uses preferably statistical methods in order to output values such as variances, scattering, mean values and the like.

Figure 2:
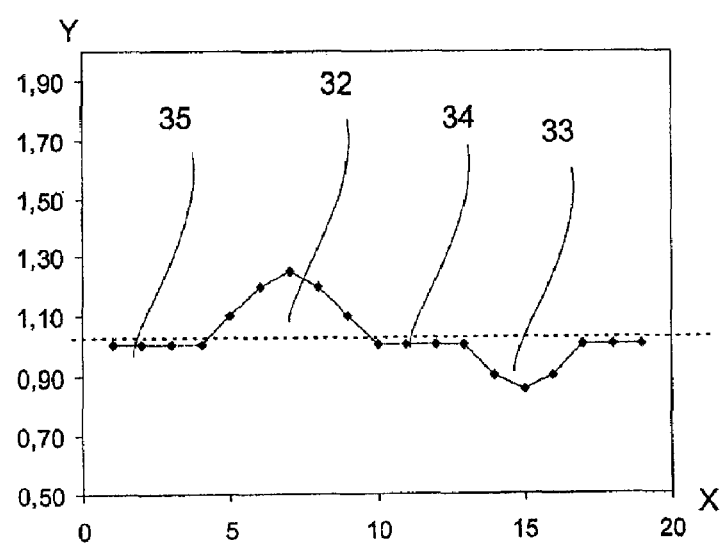

Further advantages and embodiments emerge from the appended drawings:

FIG. 1 shows a schematic diagram of an apparatus according to the invention for examining surface properties, and FIG. 2 shows an example of a series of measurements which can be recorded by means of the apparatus according to the invention.

FIG. 1 shows a schematic partial diagram of an apparatus (10) according to the invention for determining surface properties. Said apparatus has a radiation device 1 with a radiation source 2. In this embodiment, the radiation source is a white light-emitting diode (LED). Reference number 17 denotes a delimiting element such as, in particular but not exclusively, a screen for producing directional radiation which is directed onto the surface 5 to be examined. Reference numbers 15 and 14 denote diffraction elements such as lenses, which serve to focus or project the radiation emitted by the radiation device 1 and returned by the surface 5, including in the direction of the detector device 20.

Before it strikes the radiation detector device 20, the radiation passes through a delimiting element 18 in this embodiment, for example a screen and a filter 19. As mentioned above, this filter serves to block individual radiation components and to let other components pass through onto the radiation detector device 20.

Reference numbers 4 and 12 denote movement devices or wheels which are arranged on a frame 3 and by means of which the entire apparatus can be moved relative to the surface 5. The front wheel 4 has a path length measurement device 6. In this embodiment, the path length measurement device has radiation elements (not shown) and photocells and a code disc arranged between these radiation elements and the photocells. At certain frequencies, light strikes the photocell through suitable openings in the code disc between the radiation device and the photocell, as a result of which voltage pulses are generated. The path travelled relative to the surface can be determined from the frequencies and from the respective sequences of these voltage pulses. It is also possible by means of this path length measurement device 6 to determine the movement direction of the apparatus relative to the surface. Instead of the optical path length measurement device described here, however, use could also be made of inductive elements for the movement measurement device.

The radiation detector device 20 is connected to a processor device 21 which by means of a memory device 22 stores the values output by the detector device. In addition, the processor device is also connected to the path length measurement device 6, in order in this way to be able to assign the values output by the radiation detector device 20 to the values measured by the path length measurement device.

By virtue of this assignment, respective pairs of values can be created which contain on the one hand the location on the surface and on the other hand the measured value. Furthermore, a comparison value for the individual measured values can be output by means of the processor device 21, as will be explained in detail below.

Reference number 26 denotes a further radiation device, for example a laser, which irradiates radiation onto the surface 5, said radiation being oriented at a predefined angle. The further detector device 27 detects the radiation reflected by the surface. Preferably, the detector device 27 has a detection element which is suitable for detecting the radiation in a locally resolved manner. As mentioned above, the position of the apparatus as a whole relative to the surface 5 can be determined and if necessary corrected by means of the devices 26 and 27.

Reference number 24 denotes a layer thickness measurement device which determines the layer thickness of the surface to be examined. Preferably, a layer thickness measurement can be performed essentially at the same time as an optical measurement, wherein with particular preference the measurements are carried out at the same measurement location. The layer thickness measurement device is also connected to the processor unit 21 and the memory device 22, in order that the layer thickness data of the layer thickness measurement device 24 can be assigned to a specific location in addition to optical data of the detector device 20. However, the measured layer thicknesses and the optical properties can also be assigned to one another by means of the processor device in such a way that they each correspond to the same measurement locations. In this way, a more accurate image of the surface conditions can be determined.

Besides the radiation devices and radiation detector devices shown here, other radiation devices and radiation detector devices may also be provided at other angles. For the measurement in question here, a radiation detector device is preferably provided which allows only an integrative determination of the intensity which strikes it. However, it would also be possible to provide a radiation detector device which also allows a locally resolved determination of the radiation. However, in this case, the locally resolved values output by such a radiation detector device would preferably be integrated in order to achieve an overall image of the intensity.

Preferably, the illustrated radiation devices and radiation detector devices are accommodated in a common housing 31. Depending on the use example, this may be a housing with reflective properties which projects diffuse light onto the surface. In addition, a housing with an essentially absorbent inner coating may also be provided.

In the embodiment shown here, the radiation device is arranged at an angle of $\alpha=45°$ with respect to the central vertical line M. The radiation detector device is arranged at an angle of $\beta=30°$ with respect to the central vertical line M. However, other angles with respect to the central vertical line, and in particular small angles, are also conceivable. The radiation detector device could also be provided at an angle of $-30°$ with respect to the central vertical line, that is to say on the opposite side with respect to the central vertical line. During the measurement, it should be ensured that the radiation detector device is not arranged in the vicinity of the reflection angle with respect to the radiation device 1, since otherwise essentially the reflected light and not the scattered light would be detected.

Reference number 8 denotes a rubber coating applied to the wheel 4 so that, when the apparatus is moved relative to the surface 5, said surface is not damaged and on the other hand the wheel moreover does not slip on the surface, as this would falsify the distance measurement.

FIG. 2 shows an example of a fictitious series of measurements recorded using the apparatus of FIG. 1. In said figure, arbitrary units of length are plotted on the X-axis and arbitrary intensity values are plotted on the Y-axis. In this case, the intensity values are standardized to the value 1, that is to say the value 1 reflects the desired intensity.

In the example shown here, as a result of non-uniformities, the intensity values increase in a region between 5 and 10 on the X-axis and decrease in a region around the value 15. The areas 32 and 33 thus indicate those areas of the surface in which there is a non-uniform coating, whereas the coating is uniform in the areas 34, 35. The arithmetic mean value for all the measured values would be 1.025 in the present example, although this value does not provide much information about the uniformity of the coating but rather merely indicates that the mean value differs slightly upwards from a desired value.

Therefore, the variance for example is used as a measure of the non-uniformity, said variance assuming a value of 0.1925 in this case. Ideally the variance is 0, that is to say in this case the coating would be uniformly distributed over the entire surface. From the diagram shown, it can likewise be seen in which areas the coating is non-uniform and in which areas it runs in a uniform manner.

By virtue of a large number of such measurements, a three-dimensional profile could be created, wherein a lateral offset, that is to say that area in which the apparatus according to the invention is moved in a parallel manner, is also shown on a further Z-axis (not shown). Such a three-dimensional profile could be displayed for example on an image output device, such as a monitor, and be assigned to the surface to be examined, such as a motor vehicle door for example. From such a display, the user can ascertain not just whether the layer is distributed in a uniform or non-uniform manner, but rather he can also ascertain in which areas which types of non-uniformities occur in the coating.

Another conceivable measure of the non-uniformity of the surface would also be the difference between a maximum value and a minimum value, wherein in this case measurement errors are preferably taken into account in accordance with known mathematical methods. By way of example, it is conceivable to form a mean value of the three highest values and a mean value of the three lowest values, and to respectively form the difference from these mean values, wherein this difference is likewise a measure of the uniformity of the coating over the entire surface.

Preferably, in a method according to the invention, the values output by the path length measurement device are coupled to an activation device for the radiation device. In this way, after predefined intervals, for example in each case after one complete rotation of the wheel 4, another measurement point can be recorded and stored in a manner assigned to the measurement location. This method offers the advantage that measured values are in each case recorded at equal intervals regardless of the speed at which the apparatus is guided over the surface. In this case, it is also not absolutely necessary to determine the path actually travelled, since this path is clearly defined by the spatial distance between two measurements.

On the other hand, however, temporal control may also be provided, which carries out measurements in each case after predefined time intervals, wherein the respective geometric distance between two measurement points then has to also be recorded and stored.

All of the features disclosed in the application documents are claimed as essential to the invention in so far as they are novel individually or in combination with respect to the prior art.

The invention claimed is:

1. A method for determining surface properties of coatings comprising the steps of:
    irradiation of radiation onto a first region of a surface to be examined;
    detection of at least some of the radiation irradiated onto the first region and scattered by the latter and outputting a first value characteristic of this scattered radiation;
    irradiation of radiation onto a second region of the surface;
    detection of at least some of the radiation irradiated onto the second region and scattered by the latter and outputting a second value characteristic of this scattered radiation; and
    outputting a result value which is characteristic of a relationship between the first value and the second value.

2. The method according to claim 1, wherein a distance between the first region and the second region is measured.

3. The method according to claim 1, wherein the radiation is irradiated successively onto a large number of different regions of the surface.

4. The method according to claim 1, wherein the surface is radiated at least intermittently from a device that is movable relative to the surface essentially along a substantially straight line.

5. The method according to claim 1, wherein the result value is selected from a group of result values selected from the group consisting of arithmetic mean values, geometric mean values, scatterings, variances, differences, differential quotients, maxima, minima and combinations thereof.

6. The method according to claim 1, wherein the characteristic property of the radiation is selected from a group of properties selected from the group consisting of the intensity, the wavelength, the polarization and combinations thereof.

7. The method according to claim 1, wherein all characteristic values are stored in a memory device, with an allocation to the region of the surface measured.

8. The method according to claim 1, wherein a layer thickness of the surface to be examined is determined.

9. An apparatus for determining surface properties of coatings with at least one radiation device with at least one radiation source, which emits radiation onto a surface to be examined, at least one radiation detector device which detects at least some of the radiation that has been emitted by the at least one radiation device and has then been scattered by the measurement surface, and outputs at least one measured signal which is characteristic of the scattered radiation, and a processor device which compares at least two measured signals output by the measurement device, which signals correspond to different locations on the surface, and output a value characteristic of this comparison.

10. The apparatus according to claim 9, wherein the apparatus has a movement device in order to move the apparatus relative to the surface along a predefined movement direction which is preferably essentially rectilinear.

11. The apparatus according to claim 9, wherein the movement device involves at least one wheel arranged on the apparatus.

12. The apparatus according to claim 9, wherein a memory device is provided to store measured signals or values derived from these measured signals.

13. The apparatus according to claim 9, wherein the radiation device is arranged at a predefined angle with respect to the surface to be examined.

14. The apparatus according to claim 13, wherein the predefined angle is 35°.

15. The apparatus according to claim 9, wherein a plurality of radiation detector devices is provided which are arranged at different angles with respect to the surface.

16. The apparatus according to claim 9, wherein at least one radiation detector device is arranged at an angle of essentially 35° with respect to the surface.

17. An apparatus according to claim 9, wherein a plurality of radiation devices is arranged essentially perpendicular to the movement direction of the apparatus.

18. The apparatus according to claim 9, wherein a plurality of radiation detector devices is arranged essentially perpendicular to the movement direction of the apparatus.

19. The apparatus according to claim 9, wherein the apparatus has a path length measurement device to determine the length of the path travelled relative to the surface.

20. The apparatus according to claim 9, wherein at least one radiation device has at least one radiation source which is selected from a group of radiation sources comprising thermal radiation sources, said group consisting of: incandescent lamps, halogen lamps, coherent and non-coherent semiconductor radiation sources, gas discharge radiation sources, lasers, and combinations thereof.

21. The apparatus according to claim 9, wherein a layer thickness measurement device is provided.

22. The apparatus according to claim 9, wherein the apparatus has at least one filter element for selecting a predefined component of the radiation.

23. The apparatus according to claim 9, wherein a plurality of first radiation devices is provided which are arranged at predefined positions with respect to the measurement surface.

24. The apparatus according to claim 9, wherein a calibration device is provided which allows the apparatus to be oriented with respect to the surface.

* * * * *

UNITED STATES PATENT AND TRADEMARK OFFICE
CERTIFICATE OF CORRECTION

PATENT NO.         : 7,468,800 B2                                        Page 1 of 1
APPLICATION NO.    : 11/421023
DATED              : December 23, 2008
INVENTOR(S)        : Schwarz et al.

It is certified that error appears in the above-identified patent and that said Letters Patent is hereby corrected as shown below:

The following cited references listed on the title page of the patent should be enter as follows:

| | | |
|---|---|---|
| 2005/0073688 | 4/2005 | Sperling |
| 2005/0046870 | 3/2005 | Lex |
| 2005/0030542 | 2/2005 | Schwarz |

Signed and Sealed this

Fourteenth Day of July, 2009

JOHN DOLL
*Acting Director of the United States Patent and Trademark Office*